United States Patent [19]

Sherman

[11] Patent Number: 5,520,928
[45] Date of Patent: May 28, 1996

[54] PHARMACEUTICAL COMPOSITION OF TICLOPIDINE HYDROCHLORIDE

[76] Inventor: Bernard C. Sherman, 50 Oldcolony Road, Willowdale, Ontario, Canada, M2L 2K1

[21] Appl. No.: 127,379

[22] Filed: Sep. 28, 1993

[51] Int. Cl.$^6$ .......................................... A61K 9/20
[52] U.S. Cl. ................. 424/464; 424/461; 424/488; 424/480
[58] Field of Search ............................ 424/464, 461, 424/490, 489

[56] References Cited

U.S. PATENT DOCUMENTS

| | | | |
|---|---|---|---|
| 4,591,592 | 5/1986 | Chowhan | 549/74 |
| 4,702,918 | 10/1987 | Ushimaru et al. | 424/461 |
| 5,017,383 | 5/1991 | Ozawa et al. | 424/490 |
| 5,041,430 | 8/1991 | Addicks et al. | 514/161 |

*Primary Examiner*—Thurman K. Page
*Assistant Examiner*—William E. Benston, Jr.
*Attorney, Agent, or Firm*—Nixon & Vanderhye

[57] ABSTRACT

A pharmaceutical composition which comprises ticlopidine hydrochloride together with stearic acid and other suitable pharmaceutical excipients, and which does not contain any organic acid other than stearic acid.

6 Claims, No Drawings

PHARMACEUTICAL COMPOSITION OF TICLOPIDINE HYDROCHLORIDE

BACKGROUND OF THE INVENTION

1. Field of the Invention

This invention relates to stabilization of a pharmaceutical composition containing ticlopidine hydrochloride. The stabilization is achieved using stearic acid, which also serves as a lubricant.

2. Prior Art

For ease of administration of a drug, a drug is often made into the form of a tablet or capsule. Invariably, in order to make a drug into a tablet or capsule, it is necessary to use additional ingredients to serve as diluents, binders, disintegrants, lubricants and for other purposes. These additional ingredients are referred to in the pharmaceutical industry as "excipients", and are selected from substances known to be pharmacologically inactive and nontoxic.

The excipients must be selected not only to serve their desired purpose, but also such as to produce a composition that is stable. For some drugs, inclusion of certain excipients in the composition will accelerate the decomposition of the drug, and it is necessary either to exclude such excipients or to add others that will act as stabilizers and prevent the decomposition.

Ticlopidine hydrochloride is an example of a drug known to be susceptible to accelerated decomposition if certain excipients are included.

It is to be apparent to those skilled in the art that there are other such substances with similar properties.

It is to be understood that for the purposes of the specification and claims, the term active ingredient will mean such substances such as ticlopidine hydrochloride which are subject to decomposition in the presence of magnesium stearate and the like.

U.S. Pat. No. 4,591,592 to Syntex teaches that compositions containing the drug ticlopidine hydrochloride have exhibited unacceptably rapid decomposition as a result of the inclusion of certain excipients, such as gelatin, povidone and magnesium stearate. U.S. Pat. No. 4,591,592 further explains that compositions containing the drug ticlopidine hydrochloride can be stabilized by the addition of acidic compounds.

Most pharmaceutical tablets and capsules include magnesium stearate as a lubricant, and, as aforesaid, use of magnesium stearate accelerates the decomposition of ticlopidine hydrochloride.

U.S. Pat. No. 4,591,592 purports to overcome this problem by adding an acidic compound as a stabilizing ingredient. However, the use of an acid as a stablizer in addition to the use of magnesium stearate as the lubricant makes the composition more complex than desirable. Furthermore, although the compositions of U.S. Pat. No. 4,591,592 are more stable than other compositions containing ticlopidine hydrochloride, they are still less stable than desired.

One object of the present invention is to enable production of a pharmaceutical composition containing the drug ticlopidine hydrochloride in which a single substance is used as both lubricant and stablizer.

A second object of the invention is to enable production of a pharmaceutical composition containing the drug ticlopidine hydrochloride which has stability superior to the compositions of U.S Pat. No. 4,591,592.

SUMMARY OF THE INVENTION

The present invention comprises a pharmaceutically composition which comprises an active ingredient in a pharmaceutically effective dosage, stearic acid, and at least one further excipient chosen from the group comprising disintegrants, binders and diluents which are substantially free of an effective amount of organic acid other than stearic acid.

FURTHER DESCRIPTION OF THE INVENTION

The invention may be practised in the form of a tablet or capsule comprising ticlopidine hydrochloride, stearic acid as the lubricant and stabilizer, and additional excipients, e.g. binders, diluents and disintegrants. Generally pharmaceutically acceptable excipients are present to facilitate manufacture, packaging and handling of the drug and to maintain the stability of the pharmaceutical composition, e.g. stabilizer, lubricant, binder, disintegrant and diluent.

Generally ticlopidine hydrochloride will constitute about 40% to 90% of the composition by weight, stearic acid will constitute about 0.2% to 5% by weight and the other excipients about 5% to 59.8% by weight.

Compositions according to the present invention may be made by either a wet granulation or dry mix procedure.

In the wet granulation procedure, a material, e.g. lactose, is used as a diluent, and another material, e.g. povidone (polyvinyl pyrrolidinone) or hydroxypropyl cellulose, is used as a binder. The binder is dissolved in water or another solvent to form a solution, the binder solution is added to a mix of the drug, ticlopidine hydrochloride, and the diluent, and the wet mass is dried and ground into granules of desired size. The lubricant, stearic acid and a disintegrant, e.g. corn starch or croscarmellose sodium, is then added, and the resulting mix is then compressed into tablets.

A simpler and more preferred procedure than the wet granulation procedure, is a dry mix procedure, in which a single material such as microcrystalline cellulose serves as both a diluent and binder in dry form, without requiring use of water or another solvent.

The active ingredient, ticlopidine hydrochloride, is mixed with a suitable diluent, binder, e.g. microcrystalline cellulose, a lubricant, stearic acid, and a disintegrant, e.g. starch or croscarmellose sodium, and the resulting mix is compressed into tablets. In the event that the powder mix does not flow well enough for the tabletting process, the powder mix is pre-compressed by procedures known as "slugging" or "compaction", and the resultant material is ground up into free-flowing granules which are then recompressed into tablets.

The invention is further illustrated by the following example, which is not intended to limit the scope of the invention, but is given by way of illustration.

EXAMPLE 1

| Ingredients | Grams per 1000 Tablets |
| --- | --- |
| Ticlopidine hydrochloride | 250.0 |
| Microcrystalline cellulose | 130.0 |
| Stearic acid | 9.4 |
| Croscarmellose sodium | 0.6 |
|  | 390.0 |

Tablets are prepared as follows. The above ingredients are mixed in a ribbon mixer or other suitable mixer. The mixed powder is compressed into slugs, which are then ground up into free-flowing granules. The granules are then recompressed into tablets at a weight of 390 mg per tablet.

The mix of Example 1 can also be used to fill hard gelatin capsules.

The stability of tablets made according to Example 1 was compared with the stability of commercially available tablets made in accordance with the invention of U.S. Pat. No. 4,591,592, which are sold under the trade-mark "TICLID"*.

* - Registered Trade-mark

Tablets of Example 1 and TICLID* tablets were both stored at 55° C. for a period of two weeks, after which samples of both tablets were analyzed for the presence of a compound known to result for the decomposition of ticlopidine hydrochloride. It was found that the tablets of Example 1 had substantially less of the said compound that did TICLID*, indicating that the composition of Example 1 is substantially more stable than TICLID*.

* - Registered Trade-mark

Although specific embodiments of the present invention have been described above, it will be evident that various changes may be made within the spirit and scope of this invention.

The embodiments of the invention in which an exclusive property or privilege is claimed are defined as follows:

1. A stable pharmaceutical composition which comprises:
   (i) 35–95% by weight of an active agent,
   (ii) at least 0.2% by weight of a lubricate and stabilizer,
   (iii) a pharmaceutically acceptable disintegrant and binder,
   wherein said active agent consists of ticlopidine hydrochloride, and
   wherein said lubricant and stabilizer consist essentially of stearic acid.

2. The composition of claim 1 which is free of metal stearates.

3. The composition of claim 1 wherein said stearic acid is present in an amount of 0.2%–5% by weight.

4. The composition of any of claims 1 to 3 wherein said disintegrant and binder comprise microcrystalline cellulose.

5. The composition of claim 3 wherein said disintegrant and binder comprises croscarmellose sodium.

6. A pharmaceutical composition comprising:
   (i) an active agent (40–90% by weight),
   (ii) a lubricant and stabilizer (at least 0.2% by weight), and
   (iii) a pharmaceutically acceptable disintegrant and binder,
   wherein said active agent consists essentially of ticlopidine hydrochloride, and
   said lubricant and stabilizer consists essentially of stearic acid.

* * * * *

UNITED STATES PATENT AND TRADEMARK OFFICE
CERTIFICATE OF CORRECTION

PATENT NO. : 5,520,928

DATED : May 28, 1996

INVENTOR(S) : SHERMAN

It is certified that error appears in the above-indentified patent and that said Letters Patent is hereby corrected as shown below:

Column 4, line 1, change "lubricate" to --lubricant--;

line 16, change "comprises" to --further comprise--; and line 24, change "consists" to --consist--.

Signed and Sealed this

Twenty-second Day of October, 1996

Attest:

BRUCE LEHMAN

*Attesting Officer*    *Commissioner of Patents and Trademarks*